United States Patent
Lawless et al.

(10) Patent No.: US 6,494,694 B2
(45) Date of Patent: Dec. 17, 2002

(54) DISPOSABLE INFUSION CASSETTE WITH LOW AIR BUBBLE RETENTION AND IMPROVED VALVES

(75) Inventors: Mike W. Lawless, Poway, CA (US); Alex P. Soberon, San Diego, CA (US); Scott M. Defenbaugh, Temecula, CA (US); John D. Gjata, Encinitas, CA (US); David Johnston, Vernon Hills, IL (US); Robert Brose, Beach Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/842,529

(22) Filed: Apr. 25, 2001

(65) Prior Publication Data
US 2002/0159900 A1 Oct. 31, 2002

(51) Int. Cl.[7] .................................................. F04B 43/00
(52) U.S. Cl. ...................... 417/479; 604/153; 137/512.4
(58) Field of Search ................................. 417/478, 479; 604/153; 137/512.4, 855, 856

(56) References Cited

U.S. PATENT DOCUMENTS

| | | | |
|---|---|---|---|
| 5,378,126 A | * 1/1995 | Abrahamson et al. | 417/413.1 |
| 5,462,256 A | 10/1995 | Minick et al. | 251/331 |
| 5,586,868 A | 12/1996 | Lawless et al. | 417/53 |
| 5,603,613 A | * 2/1997 | Butterfield et al. | 417/474 |
| 5,728,069 A | * 3/1998 | Montevecchi et al. | 604/153 |
| 6,165,154 A | * 12/2000 | Gray et al. | 604/153 |

* cited by examiner

Primary Examiner—Cheryl J. Tyler
(74) Attorney, Agent, or Firm—Brian R. Woodworth

(57) ABSTRACT

A disposable cassette for use with a medical infusion pump. An elastomeric membrane is captured between a facing member and a base of the cassette and is displaced into a pumping chamber. The elastomeric membrane includes a generally T-shaped lip, and corresponding grooves are provided on the facing member and base. As the cassette is assembled, an interference fit between the lip and the grooves causes the membrane to stretch taut and to be securely anchored, eliminating a break-in period when the cassette is initially used. "Lobes" of increased thickness provided on the undersurface of a portion of the elastomeric membrane overlying the pumping chamber reduce the residual volume of the pumping chamber, thereby reducing the volume of air retained within the chamber and increasing the accuracy of the cassette. The lobes also sweep air bubbles from the sides of the pumping chamber during operation, further reducing air bubbles retained in the pumping chamber. A distal tube support retains a distal fluid line between air or pressure sensors included on a pump drive mechanism, thus reducing the likelihood of sensing errors. Inlet and outlet valve flaps and corresponding seating surfaces included in the base are configured to provide quieter operation, further reduce the residual volume of the pumping chamber, increase fluid velocity through the outlet valve to sweep air bubbles from the pumping chamber, and protect against a "blown" inlet valve.

38 Claims, 8 Drawing Sheets

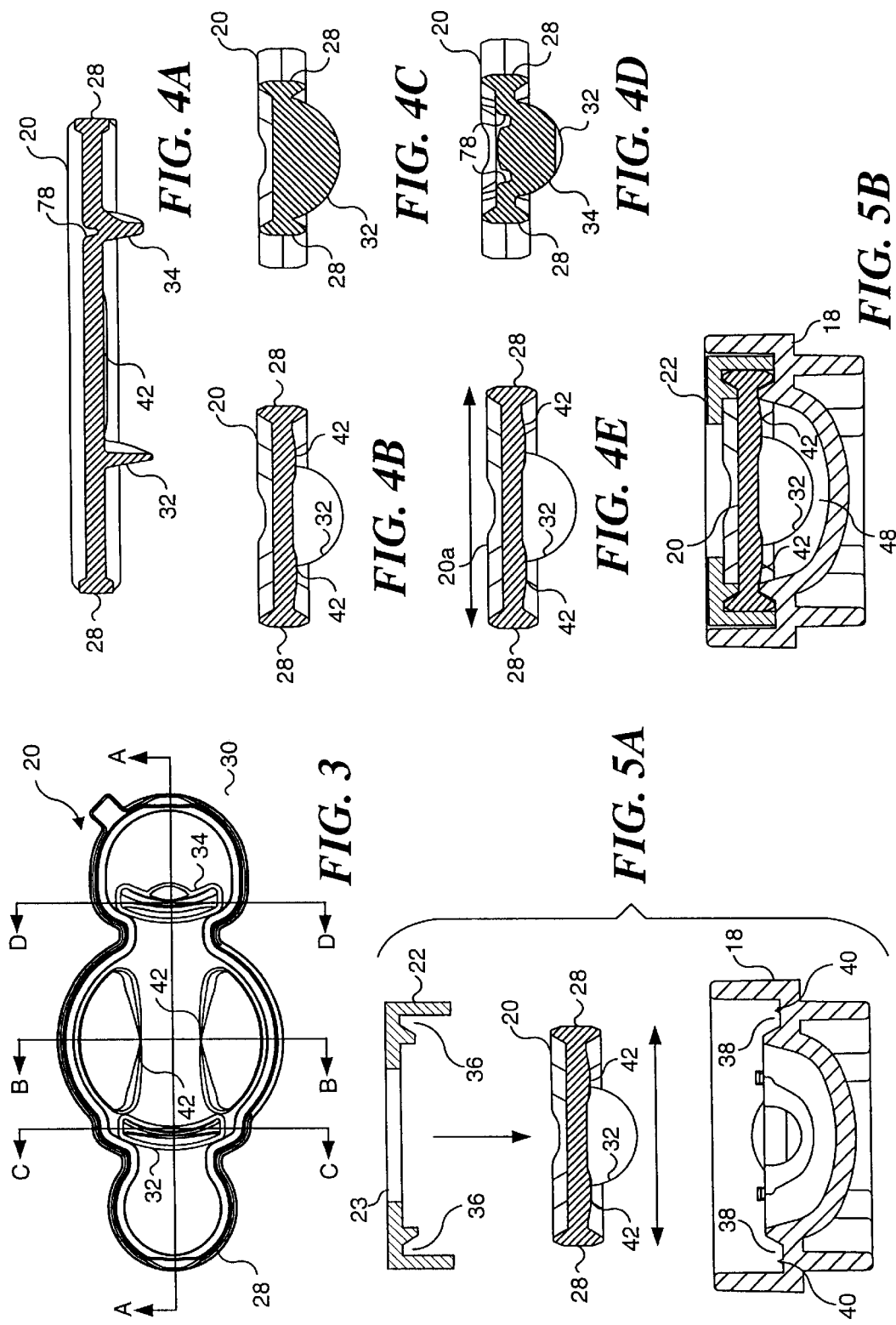

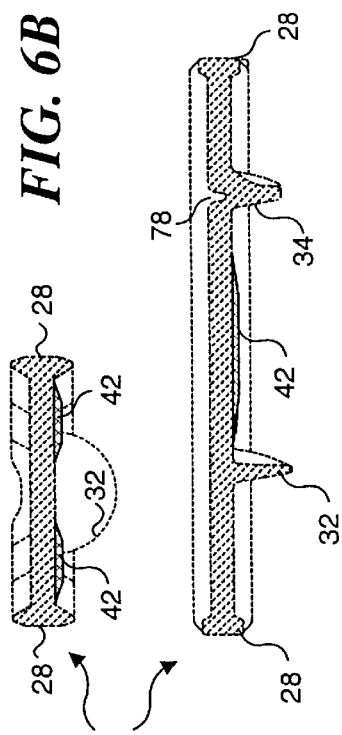
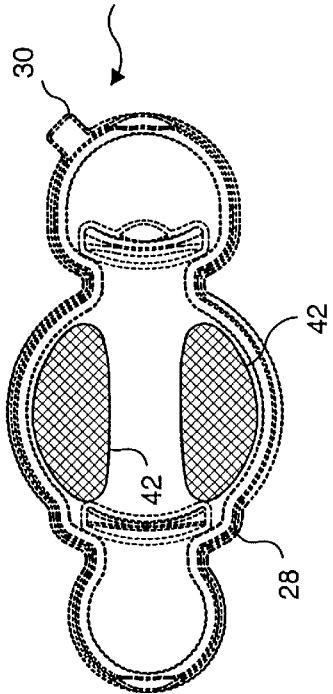
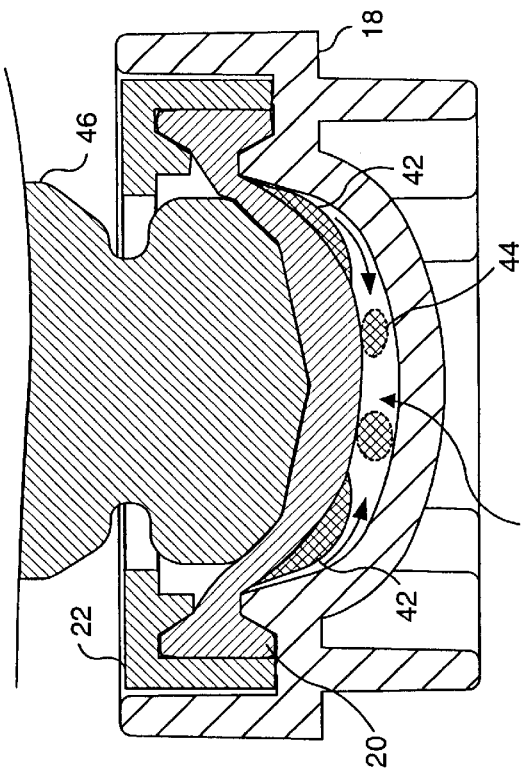
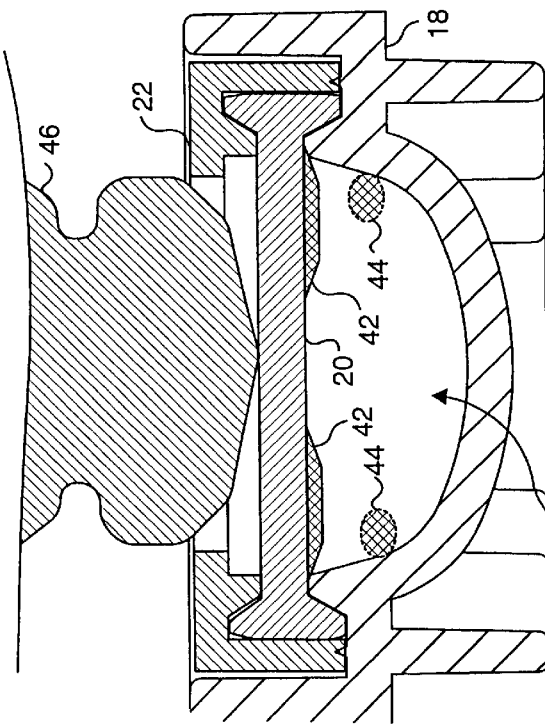

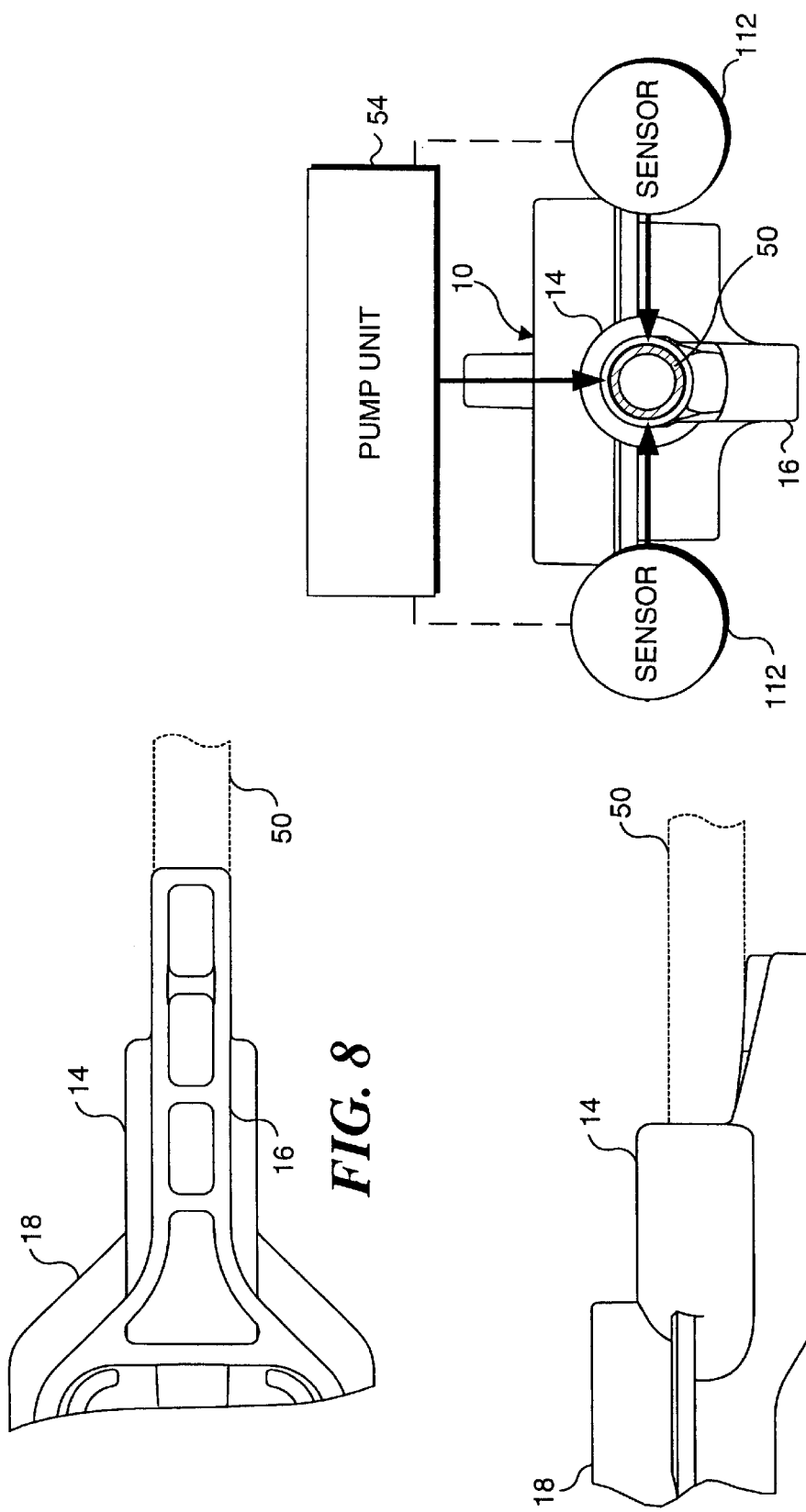

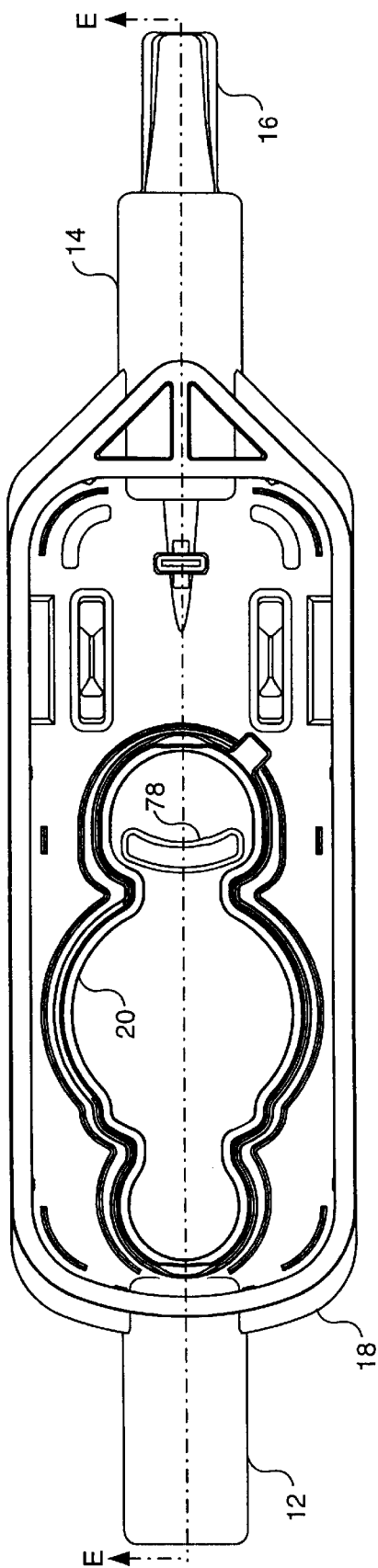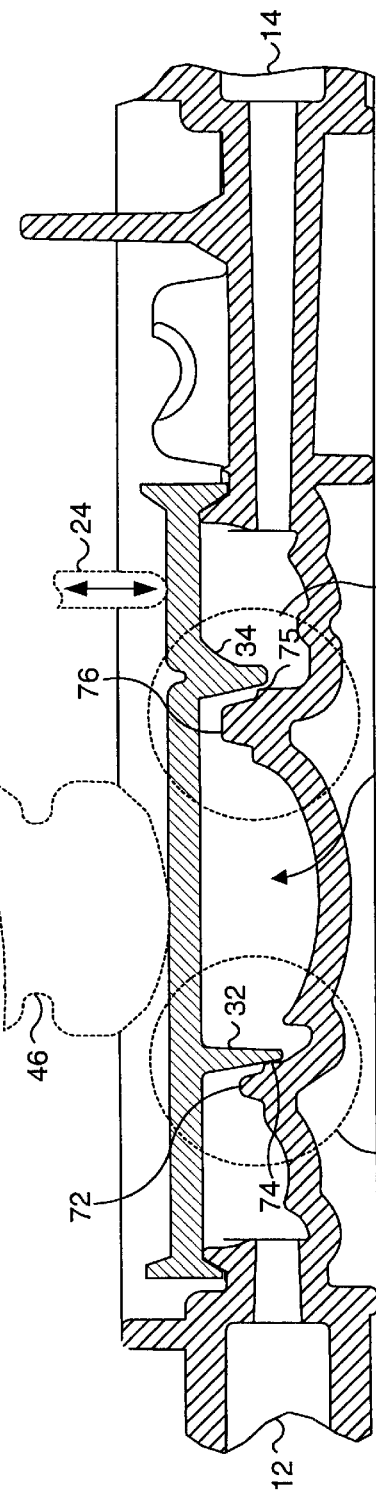
FIG. 11
FIG. 12

DISPOSABLE INFUSION CASSETTE WITH LOW AIR BUBBLE RETENTION AND IMPROVED VALVES

FIELD OF THE INVENTION

The present invention generally relates to a positive displacement volumetric infusion cassette pump, and more specifically, to a disposable cassette adapted for use with such a pump, the cassette having an elastomeric membrane that is displaced by a plunger into a cavity to pump fluid and including integral inlet and outlet valve components formed on a surface of the elastomeric membrane.

BACKGROUND OF THE INVENTION

Various types of pumps are used by medical personnel to infuse drugs into a patient's body. Of these, cassette infusion pumps are often preferred because they provide a more accurately controlled rate and volume of drug infusion than other types of infusion pumps. A cassette pump typically employs a disposable plastic cassette coupled between a proximal liquid line extending from a drug reservoir or source, and a distal fluid line that is coupled to the patient's body. The cassette is adapted to engage and be driven by a pump mechanism that includes a control and an interface for setting the desired flow rate, volume of fluid, and other parameters that control the infusion process.

In one prior art design of a disposable cassette, the cassette comprises a plastic shell or housing having a facing member joined to a base. The cassette is inserted into an appropriate receptacle in a pump chassis that typically includes a microprocessor controller and a motor or solenoid-actuated driver. A thin elastomeric sheet or membrane is encapsulated between the two sections. Inlet and outlet flapper valves are formed on one side of this elastomeric membrane and seal against adjacent surfaces formed on the base. These flapper valves are actuated in response to fluid pressure and the force applied by a plunger against the elastomeric membrane. As the plunger withdraws following a pumping stroke, the inlet flapper valve opens, enabling liquid to flow from the drug reservoir through an inlet port of the cassette and into a pumping chamber defined in the base and covered by the elastomeric membrane. The plunger actuated by the motor or solenoid in the pump driver displaces the elastomeric membrane into the pumping chamber, opening the outlet flapper valve and forcing liquid under pressure from the pumping chamber, through an outlet port. The pump chassis thus provides the driving force that pumps liquid through the cassette. In addition, the pump chassis normally includes one or more pressure sensors and air bubble sensors for monitoring and controlling the drug infusion process to protect against potential problems that may arise during delivery of a medicinal liquid to a patient.

Cassette infusion pumps have been widely adopted by the medical profession, which uses millions of such disposable cassettes per year. As is common with other high volume production items, manufacturers continually strive to improve their products. For instance, in prototype unit developed by applicant as a replacement for an existing product, it was observed that during operation, the prototype cassette produced a surprising level of audible noise. Much of this undesirable noise can be attributed to the operation of the flapper valves. Also, in prior art cassettes, when exposed to higher than optimal pressure conditions, the flapper valves can be "blown," that is, the flapper valves can be forced beyond their sealing surfaces by excess pressure. It would therefore be desirable to provide a cassette that includes valve elements that produce substantially less audible sound when operating, and are much less susceptible to being "blown."

Improving the reliability of disposable cassettes is also a goal of both end users and manufacturers. As noted above, disposable cassettes frequently are adapted to engage with air or pressure sensors included on the pumping mechanisms used, which can trigger an alarm to alert an operator of an undesirable or unsafe operating condition. The disposable cassettes generally include sensor ports that enable the sensors disposed on the pumping mechanism to monitor a parameter such as pressure or the presence of air in a fluid line. Including the sensor ports within a disposable cassette can increase the size and cost of the cassette. It would be desirable to eliminate any air sensor ports from the disposable cassette, so that the size and cost of disposable cassettes can be substantially reduced. Instead, the air sensors should be positioned to sense parameters relating to the presence of air contained within a tube set that is connected to the outlet port of the cassette. For proper operation, it is important that the positional relationship between the external air sensors and tubing be stable and consistent, because if the tubing moves relative to the sensors, false alarms can be generated, and/or errors in the monitored parameters can result. It would thus be desirable to provide a cassette that incorporates elements, which ensure the fluid tubing remains in a predetermined position relative to external air sensors, to reduce the possibility of erroneous sensor readings and false alarms due to movement of the fluid tubing relative to the sensors.

Another goal in the further development of disposable cassettes is improving the accuracy with which a medicinal liquid is delivered. It is well understood that air bubbles within cassettes are undesirable for several reasons. While gross amounts of air bubbles, such as levels that pose a risk to a patient's health by causing an embolism, are not much of a risk in such systems, even smaller volumes of air retained within a cassette pumping chamber can adversely impact the accuracy with which medicinal liquid is delivered to a patient. Prior art cassettes typically attempt to prevent air bubbles in the system by using a combination of an integral air trap and appropriate cassette priming procedures. While air traps and proper priming techniques generally avoid the delivery of large volumes of air that can pose a health risk, smaller volumes of air bubbles that become trapped within the cassette are more difficult to remove. When air bubbles are present within the pumping chamber, accuracy is affected in several ways.

The volume of the pumping chamber is a critical parameter in the algorithm controlling the pump to achieve accuracy in delivering a desired volume of medicinal liquid. The presence of air bubbles within the pumping chamber effectively reduces the volume of the pumping chamber, so that less than a desired volume of fluid will be delivered each pump cycle. Increasing the complexity of this problem is that pressure conditions within the pumping chamber vary during the pumping cycle, so that the actual volume of a fixed mass of air within the pumping chamber is not constant. Thus, the actual volume of fluid delivered cannot be accurately determined and compensated, because the volumetric error caused by the mass of air trapped within the pumping chamber is not constant. Accordingly, it would be desirable to provide a disposable cassette including elements that reduce the generation and/or retention of air bubbles within the pumping chamber, and elements that promote the removal of any air bubbles that are present in the pumping chamber.

Another aspect of the accuracy of prior art disposable cassettes relates to the elastomeric membrane. In prior art cassettes, the elastomeric membrane typically requires a break-in period the first time the cassette is used. This break-in period is required to enable the elastomeric membrane to reach an equilibrium, so that the repetitive manipulation of the membrane during successive pumping cycles produces repeatable results. Generally, the break-in period is required to enable the membrane to become seated with respect to the facing member and base of the housing that retain the elastomeric membrane, so that repeated manipulation of the membrane does not result in any further stretching or movement of the membrane relative to the housing.

Clearly, it would be desirable to provide a disposable cassette that reduces operating noise, that provides enhanced protection against valve deformation (failure) under excessive pressure conditions, that substantially reduces false alarms and increases the reliability of external sensor data, that provides increased accuracy by reducing the volume of air trapped in the pumping chamber, and by eliminating the need for a break-in period of the elastomeric membrane. The prior art does not provide such a disposable cassette.

SUMMARY OF THE INVENTION

The present invention defines a cassette that is adapted to engage a drive mechanism, for use in infusing a fluid into a patient. The cassette includes a housing having a base on which is mounted a facing member. An elastomeric membrane is secured between the facing member and the base. A fluid path between the elastomeric membrane and the base extends through the cassette between an inlet port and an outlet port. The fluid path includes an inlet passage coupled in fluid communication with the inlet port, an outlet passage coupled in fluid communication with the outlet port, and a pumping chamber disposed between the inlet passage and the outlet passage. When the elastomeric membrane is displaced into the pumping chamber, it is adapted to force a fluid from the pumping chamber. The elastomeric membrane has a substantially T-shaped lip extending around and proximate its peripheral edge. The T-shaped lip is captured in an interference fit within a groove formed in opposed surfaces of the facing member and the base so that the elastomeric membrane is stretched taut as the facing member is joined to the base. The groove includes inclined surfaces that are in interference with corresponding inclined surfaces on the T-shaped lip. When the facing member is seated onto and joined to the base with the lip of the elastomeric membrane captured in the groove, a tension in the elastomeric membrane produced by the interference fit due to an interaction of the inclined surfaces of the groove and the T-shaped lip compensates for any inelastic deformation of the elastomeric membrane occurring when the elastomeric membrane is displaced into the pumping chamber. This compensation thus minimizes errors in achieving a desired volume of a fluid infused by the cassette.

In at least one embodiment, an extent of an area of the elastomeric membrane defined by the inclined surfaces of the T-shaped lip is less than an extent of an area defined in the base and facing member by the inclined surfaces of the groove formed therein. Preferably, the facing member is seated against and ultrasonically welded to the base while the T-shaped lip of the elastomeric membrane is compressed in the interference fit within the groove.

Also, the fluid path preferably further includes an inlet valve disposed between the inlet passage and the pumping chamber, and an outlet valve disposed between the pumping chamber and the outlet passage. The inlet valve includes an inlet valve surface formed in the base, and an inlet valve flap formed on an undersurface of the elastomeric membrane that seats against the inlet valve surface when the inlet valve is closed. Similarly, the outlet valve includes an outlet valve surface formed in the base, and an outlet valve flap formed on the undersurface of the elastomeric membrane that seats against the outlet valve surface when the outlet valve is closed. In at least one embodiment, the inlet valve surface on the base includes a ramp, and the inlet valve flap is substantially thinner at a depending tip thereof than a depending tip of the outlet valve flap. The depending tip of the inlet valve flap is also substantially thinner than a portion of the inlet valve flap where it is joined to the undersurface of the elastomeric membrane. In this manner, the inlet valve and the outlet valve are configured to substantially reduce audible noise produced as the inlet valve and the outlet valve open and close. The thickness of the outlet valve flap and its disposition relative to the outlet valve surface preferably provide a biasing force tending to keep the outlet valve closed until a fluid pressure in the pumping chamber reaches a predetermined level. This biasing force is selected to prevent siphon free flow of a fluid through the cassette.

The base further preferably includes a tube support member that extends beyond the outlet port and is adapted to support a tube that is coupled to the outlet port to receive fluid forced from the cassette. The tube support member ensures that the tube remains statically positioned relative to an air-in-line sensor provided on the drive mechanism during use of the cassette.

Another aspect of the present invention is directed to a method for mounting an elastomeric membrane in a cassette used for infusing a fluid into a patient, so as to pre-load the elastomeric membrane under an outwardly directed tension. The steps of the method include providing a generally T-shaped lip extending around and proximate to a peripheral edge of the elastomeric membrane. The T-shaped lip has inclined surfaces extending from where the T-shaped lip extends from a generally planar surface of the elastomeric membrane toward distal tips of the T-shaped lip. Other steps of the method include providing a base and a facing member for the cassette that each include a groove with inclined surfaces shaped and sized to receive a different distal tip of the T-shaped lip in an interference fit.

The steps of the method further include positioning a distal tip of the T-shaped lip of the elastomeric membrane in the groove formed in one of the base and the facing member, then seating the groove formed in the other of the base and the facing member onto an opposite distal tip of the T-shaped lip, and pressing the base and the facing member toward each other until the T-shaped lip seats within the grooves formed in the base and the facing member. The interference fit between the inclined surfaces of the grooves and the T-shaped lip draws the elastomeric membrane taut under a pre-load tension. The next step involves joining the base and the facing members together while the elastomeric membrane is taut, so that the elastomeric membrane is captured under the pre-load tension between the facing member and the base.

Preferably, the step of joining the base and the facing members involves ultrasonically bonding the facing member to the base, or alternatively, the base and facing member are joined using thermal bonding or adhesive bonding. Also, the step of providing the T-shaped lip preferably includes the step of molding the lip around a peripheral edge of the elastomeric membrane. An area of the elastomeric membrane within the lip is less than an area circumscribed by the grooves formed in both the base and the facing member.

Another aspect of the present invention is directed to a cassette that includes an elastomeric membrane having lobes adapted to sweep air bubbles from the sides of the pumping chamber, thereby minimizing errors introduced by air bubbles disposed within the pumping chamber. As before, the cassette is adapted to engage a drive mechanism and is used for infusing a medicinal liquid into a patient. Also as noted above, the cassette includes a housing having a base on which is mounted a facing member. A fluid path is defined between the elastomeric membrane and the base, and extends through the cassette between an inlet port and an outlet port. The facing member is employed to secure the elastomeric membrane relative to the base, and the facing member is preferably not part of the fluid path. The fluid path includes an inlet passage coupled in fluid communication with the inlet port, an outlet passage coupled in fluid communication with the outlet port, and a pumping chamber disposed between the inlet passage and the outlet passage. When the elastomeric membrane is displaced into the pumping chamber, it forces a fluid from the pumping chamber. The elastomeric membrane has a generally planar undersurface facing toward the base, but this surface includes two lobes of increased thickness disposed above the pumping chamber, at opposite sides thereof. The increased thickness of the lobes extends into the pumping chamber so that when the elastomeric diaphragm is displaced into the pumping chamber by a drive mechanism, the lobes sweep away many air bubbles that may be retained on adjacent walls of the pumping chamber. When displaced into the pumping chamber, the lobes also preferably define a shallow elongate path through the pumping chamber between the lobes, so that a substantial portion of any air contained within the pumping chamber is carried out of the pumping chamber with the medicinal liquid being infused.

Preferably the elastomeric membrane further includes an inlet valve flap and an outlet valve flap, both of which depend from the undersurface of the elastomeric membrane. The inlet valve flap, when closed by a fluid pressure within the pumping chamber, forms a seal against an inlet valve surface formed in the base and disposed between the inlet passage and the pumping chamber. In similar fashion, the outlet valve flap when closed, forms a seal against an outlet valve surface defined in the base and disposed between the pumping chamber and the outlet passage. The inlet valve is preferably configured to be substantially thinner at a tip than where the inlet valve flap joins with a substantially planar portion of the elastomeric membrane and comprises a ramp that is inclined at an angle. The angle is selected so that in cooperation with the inlet valve flap, audible noise caused by repetitive opening and closing of the inlet valve flap relative to the inlet valve surface is substantially reduced. The outlet valve flap is preferably substantially thicker than the inlet valve flap and provides a biasing force tending to maintain the outlet valve flap sealed against the outlet valve surface until a pressure in the pump chamber exceeds a predefined level. Preferably, the predefined level is selected to prevent a siphon induced free flow of fluid through the cassette.

The base of the cassette includes a distal member that extends distally past the outlet port and is adapted to support a tube that is coupled in fluid communication with the outlet port. The support of this distal member minimizes movement of the tube relative to an air-in-line sensor that is included in the drive mechanism.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 3 is a bottom plan view of the elastomeric membrane of FIG. 2;

FIG. 4A is a cross-sectional view of the elastomeric membrane of FIG. 2 taken along section lines A—A;

FIG. 4B is a cross-sectional view of the elastomeric membrane of FIG. 2 taken along section lines B—B;

FIG. 4C is a cross-sectional view of the elastomeric membrane of FIG. 2 taken along section lines C—C;

FIG. 4D is a cross-sectional view side of the elastomeric membrane of FIG. 2 taken along section lines D—D;

FIG. 4E is a cross-sectional view of the elastomeric membrane of FIG. 2 taken along section lines B—B, illustrating an elastomeric membrane that is stretched taut when the facing member and the base are assembled on each side of the elastomeric membrane;

FIG. 5A is an exploded cross-sectional view of the elastomeric membrane of FIG. 4A, and the facing member and the base;

FIG. 5B is a cross-sectional view of the assembled cassette, illustrating an interference fit between the elastomeric membrane, and the facing member and the base;

FIG. 6A is a bottom plan view of the elastomeric membrane of FIG. 2, showing the lobes as a shaded portion for emphasis, and the balance of the elastomeric membrane in phantom view;

FIG. 6B is a cross-sectional view of the elastomeric membrane of FIG. 2, taken along section lines A—A of FIG. 3, showing the lobes as a shaded portion for emphasis, and the balance of the elastomeric membrane in phantom view;

FIG. 6C is a cross-sectional view of the elastomeric membrane of FIG. 2, taken along section lines B—B of FIG. 3, showing the lobes as a shaded portion for emphasis, and the balance of the elastomeric membrane in phantom view;

FIG. 7A is a simplified cross-sectional view of the assembled cassette of FIG. 1, illustrating a plunger passing though an opening in facing member to contact with the elastomeric membrane, lobes depending downwardly from the underside of the elastomeric membrane, and a plurality of air bubbles disposed on the sides walls of the pumping chamber;

FIG. 7B is a simplified cross-sectional view of the assembled cassette of FIG. 1, illustrating the plunger forcing the elastomeric membrane into the pumping chamber and causing the lobes to sweep the sides of the pumping chamber to displace the air bubbles;

FIG. 8 is a bottom plan view of the distal potion of the base and the distal tube support;

FIG. 9 is a side elevational view of the distal potion of the base and the distal tube support;

FIG. 10 is a schematic representation showing the positional relationships between the cassette of FIG. 1, the distal delivery tube, a pump unit for drivingly engaging the cassette, and a plurality of sensors that are mounted on the pump unit;

FIG. 11 is a top plan view of the elastomeric membrane seated in the base;

FIG. 12 is a cross-sectional view of the elastomeric membrane seated into the base taken along section line E—E in FIG. 11, showing the inlet valve, the pumping chamber, and the outlet valve;

DESCRIPTION OF THE PREFERRED EMBODIMENT

Overview of the Present Invention

Figure 1:
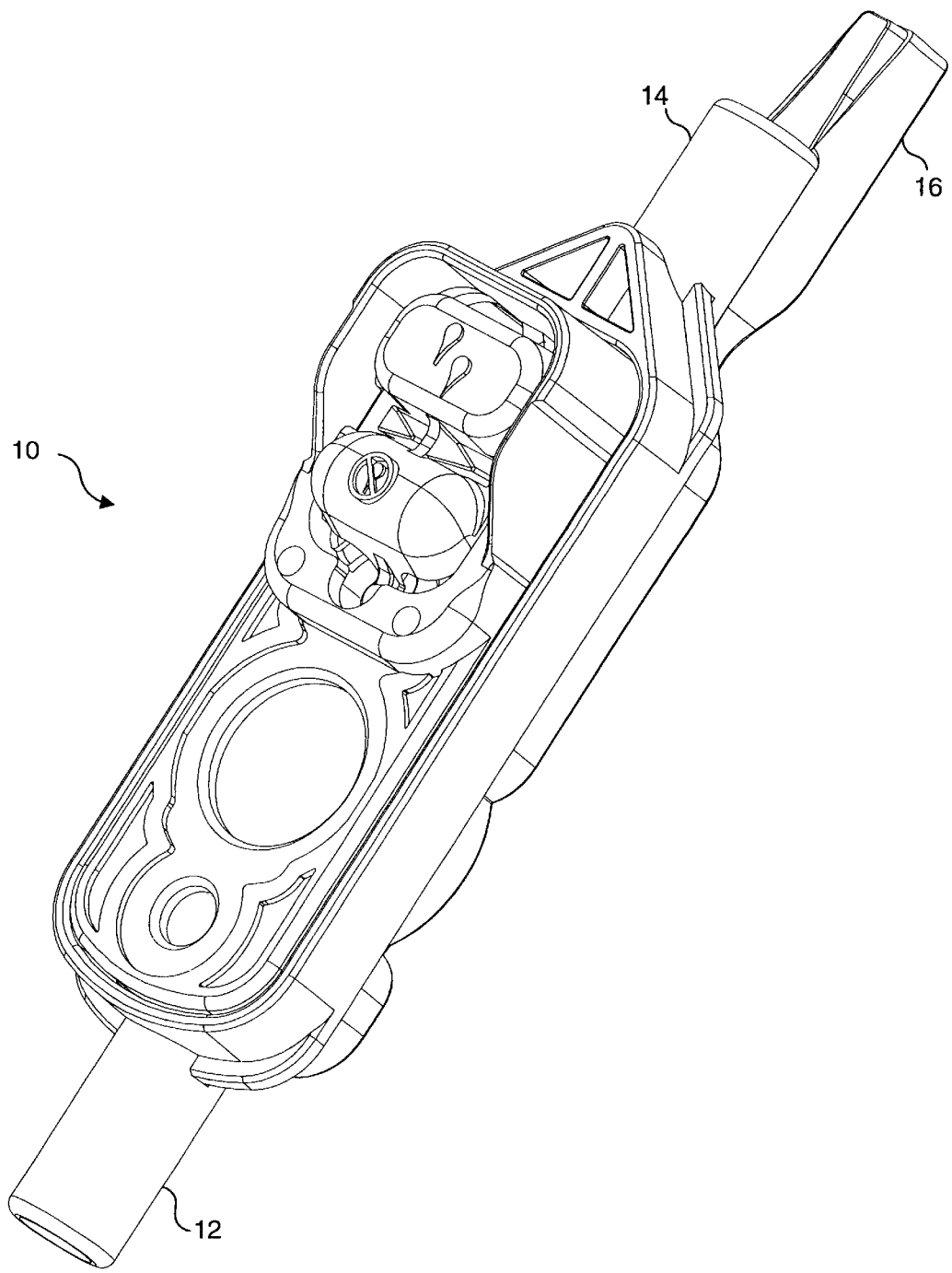
FIG. 1 is an isometric view of an assembled cassette in accord with the present invention.

The present invention employs a novel elastomeric membrane design and housing design to improve the performance of a disposable cassette type infusion pump and to better support outlet tubing. The tube support minimizes the number of false air alarms caused by improper positioning of the outlet tube. A preferred embodiment of the present invention, as disclosed below, will be used in conjunction with an appropriate infusion pump chassis. However, it should be noted that the present invention can readily be adapted for use with other types of infusion pumps. Thus, the present invention is not in any way limited to the specific design of the pump and/or cassette discussed below.

The general operation of an infusion pump that includes a plunger to displace an elastomeric membrane into a pumping chamber is well known in the art. For example, details of such a pump and cassette are described in commonly assigned U.S. Pat. Nos. 5,462,256 and 5,586,868, the disclosures and drawings of which are hereby specifically incorporated herein by reference. The following disclosure makes note of the differences between the present invention and the prior art cassettes disclosed in these two references, the following discussion should be relied upon to describe the present invention, as opposed to the disclosure in the referenced patents, where any such differences exist.

The terms "proximal" and "inlet" as used in connection with the following description and the claims that follow synonymously refer to the portion of the cassette that is coupled in fluid communication with a fluid line (or lines) that convey a fluid from a reservoir or other source. The terms "distal" and "outlet" similarly synonymously refer to the portion of the cassette that is coupled in fluid communication with a fluid line adapted to be connected to a patient, for infusing the medicinal liquid.

The present invention involves changes to the elastomeric membrane, and to the front and base of the housing relative to the corresponding elements in the above-referenced patents. These changes result in a more reliable and accurate disposable cassette. The first change relates to the fit between the elastomeric membrane and the front and base sections. While prior art membranes require a break-in period when pumping is initiated, and are subject to reduced accuracy caused by slackness in the elastomeric membrane after the break-in period, the present invention "pre-loads" the elastomeric membrane, eliminating the need for the break-in period. A second change in the design of the elastomeric membrane enables the membrane to efficiently sweep air bubbles off the sides of the pumping chamber during operation, thus reducing errors in the volume of fluid delivered caused by air bubbles retained in the pumping chamber. A third change provides better support for a distal fluid line, ensuring that it is properly positioned with respect to distal sensors that are external to the cassette, thus minimizing the likelihood of errors due to movement or due to an incorrectly positioned fluid line. A fourth change to the inlet and outlet valves and the seating surfaces incorporated into the base of the cassette results in audibly quieter operation.

FIG. 1 is an isometric view of an assembled disposable cassette 10 in accord with the present invention. Cassette 10 includes an inlet 12 and an outlet 14. Associated with outlet 14 is a distal delivery tube support 16. As noted above, one of the features of the cassette in accord with the present invention is tube support 16. As will be described in detail below, tube support 16 ensures that a distal delivery tube inserted into outlet 14 is maintained in a proper position with respect to external sensors (see FIG. 10). By providing support for a distal delivery tube (not shown) that is attached to the outlet, tube support 16 substantially reduces the number of erroneous sensor readings that might occur is the delivery tube moves during use of the cassette.

Figure 2:
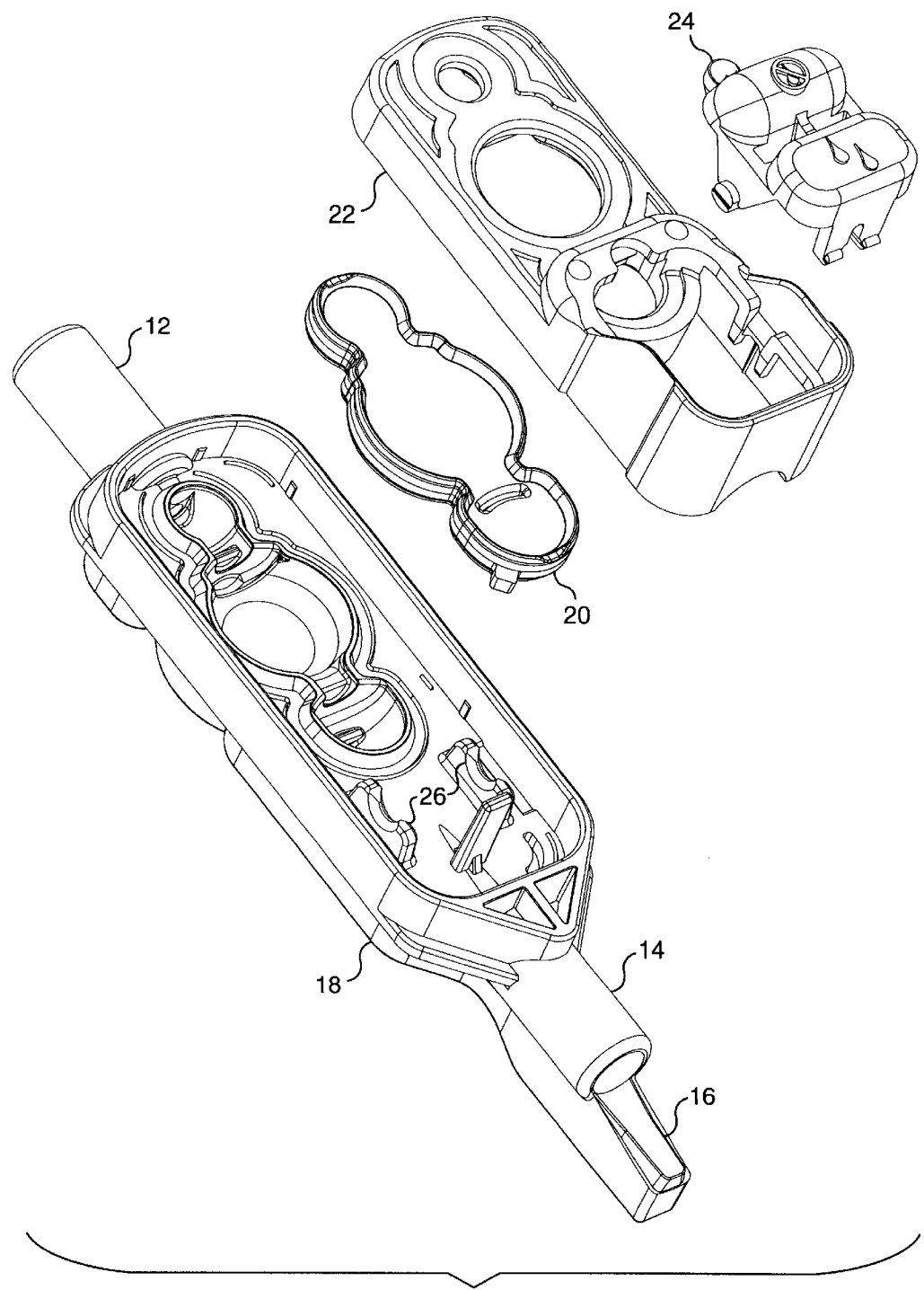
FIG. 2 is an exploded isometric view of the cassette of FIG. 1.

FIG. 2 is an exploded isometric view of cassette 10. In FIG. 2 it can clearly be seen that cassette 10 includes a base 18, an elastomeric membrane 20, and a facing member 22. A flow stop 24 pivotally engages a plurality of supports 26 that are integral to base 18. Flow stop 24 is held in place by facing member 22 when the cassette is fully assembled. It should be noted that while flow stop 24 is of slightly different design than the flow stop described in the above-referenced commonly assigned U.S. Pat. Nos. 5,462,256 and 5,586,868, the functional characteristics of flow stop 24 are unchanged from these prior art references. Accordingly, flow stop 24 need not be discussed herein in detail and generally will not be shown in the balance of the figures.

FIGS. 3–5 illustrate structural details of the facing member, the elastomeric membrane, and the base: that enable the elastomeric membrane to be pre-loaded so that a break-in period is not required for the elastomeric membrane to provide reproducible results. This problem has been solved in the present invention by including a generally T-shaped lip 28 around the peripheral edge of the elastomeric membrane, and corresponding generally T-shaped grooves 36 and 38 within the surfaces of the facing member and the base, configured and sized such that when the elastomeric membrane is placed between the facing member and base, the elastomeric membrane is stretched slightly. This slight stretching pre-loads the elastomeric membrane, making it taut, such that a break-in period is no longer required in order for the elastomeric membrane to reproducibly respond to displacement by a plunger. In the prior art, a break-in period of as much as 10 minutes was required before the elastomeric membrane became firmly seated and stopped moving.

The pre-loading of the elastomeric membrane in the present invention also compensates for any inelastic deformation of the elastomeric membrane occurring when the elastomeric membrane is displaced into the pumping chamber, to minimize errors in achieving a desired volume of a fluid infused by the cassette, as well as compensating for minor imperfections introduced during the manufacture of the elastomeric membranes. Preferably, elastomeric membrane 20 is stretched taut due to the interference fit between corresponding sloping surfaces on the T-shaped lip and grooves 36 and 38 (see FIGS. 5A and 5B) and is firmly anchored within these grooves, so that when a plunger displaces the elastomeric membrane into the pumping chamber, the elastomeric membrane does not move, but instead, remains fixed and always under a slight tension. In a preferred embodiment, the elastomeric membrane is stretched laterally by 2–3% due to the interference fit.

FIG. 3 illustrates details of elastomeric membrane 20. Generally T-shaped lip 28 extends around the periphery of elastomeric membrane 20. Since FIG. 3 is a bottom plan view of elastomeric membrane 20, inlet and outlet valve flaps 32 and 34 can readily be seen. An assembly tab 30 is disposed adjacent to the distal end of elastomeric membrane 20. Assembly tab 30 is included so that a reference is provided to facilitate properly positioning elastomeric membrane 20 in the cassette housing. While the shape of the distal portion of elastomeric membrane 20 is slightly different than the shape of the proximal portion, the inclusion of assembly tab 30 eliminates the possibility of improper assembly. Two lobes 42 are evident on each side of the central portion of the elastomeric membrane, and their significance will be discussed in detail below.

As shown in the cross-sectional views of FIGS. 4A–4D, T-shaped lip 28 extends around the periphery of the elastomeric membrane, and inlet valve flap 32 and outlet valve flap 34 depend downwardly from the undersurface of elastomeric membrane 20. The relatively greater thickness of lobes 42 on the inwardly facing surface of elastomeric membrane 20 is also evident in these views. Outlet valve flap 34 includes a central core 78, the significance of which will be discussed in detail below.

FIG. 4E shows the same cross-sectional view of elastomeric membrane as FIG. 4B. However, in FIG. 4E, elastomeric membrane 20a has been mounted between the facing member and the base, and as a result of the interference fit, is stretched slightly, such that elastomeric membrane 20a of FIG. 4E is slightly larger in area than elastomeric membrane 20 of FIG. 4B. The sloping surfaces on the inner sides of grooves 36 and 38 interact with the corresponding sloping surfaces of the T-shaped lip as the housing is assembled with the elastomeric membrane trapped between, causing the elastomeric membrane to be stretched outwardly.

Referring to FIGS. 5A and 5B, an opening 23 is provided in facing member 22, allowing a plunger driven by the pump unit (neither separately shown) to engage the exposed upper surface of elastomeric membrane 20. The facing member includes groove 36 around its periphery. Groove 36 is of a size and shape that generally corresponds to an upper half of T-shaped lip 28 of elastomeric membrane 20. Base 18 includes groove 38, which similarly extends around the periphery of base 18 and is approximately the same size and shape as groove 36. As elastomeric membrane 20 is lowered into base 18, T-shaped lip 28 of elastomeric membrane 20 engages the upper portion of groove 38. Facing member 22 is then lowered, causing groove 36 to engage the upper portion of the T-shaped lip of elastomeric membrane 20. A compressive force is applied to force facing member against base 18, fully seating the T-shaped lip within grooves 36 and 38 and causing the elastomeric membrane to stretch slightly as the interference fit is made between the T-shaped lip and the grooves in the facing member 22 and base 18. Note that base 18 includes ultrasonic beads 40, which melt when heated using ultrasound, causing facing member 22 to be welded to base 18. FIG. 5B shows facing member 22, base 18, and a stretched elastomeric membrane 20a in a fully assembled configuration. Note that a pumping chamber 48 is defined between base 18 and elastomeric membrane 20.

Another feature of the present invention involves the inclusion of thickened lobes 42 on the underside of the elastomeric membrane. Lobes 42 (see FIGS. 3, 4A, 4B, 4E, 5A, and 5B) are disposed in a portion of the elastomeric membrane that overlies the pumping chamber. The lobes are disposed along each side of the elastomeric membrane, such that when a plunger presses the elastomeric membrane into the pumping chamber, the lobes sweep the sides of the pumping chamber, forcing bubbles that have adhered to the walls of the sides of the pumping chamber into a lower central portion of the pumping chamber. The lobes define a flattened central passage through the middle of the pumping chamber at full extension of the plunger; creating a channel through which the medicinal liquid flows. Since the bubbles are swept off the sides into this lower portion of the pumping chamber by the sweeping action of the lobes, the air bubbles are more likely to be carried from the pumping chamber by the medicinal liquid flowing from the pumping chamber through this central flattened central passage when the outlet valve is open. While only slightly thicker than the other planar portions of the elastomeric membrane, empirical studies have determined that these lobes have a significant effect on removing the air bubbles from within the pumping chamber. As a consequence, much less air is retained in the pumping chamber over time.

As noted above in the Background of the Invention, air bubbles retained within the pumping chamber can induce significant errors in the accuracy of the volume of medicinal liquid delivered in prior art cassette pumps. The air bubbles that are retained occupy a volume within the pumping chamber that should be filled by medicinal liquid during each pumping stroke. Also, the volume of the air bubbles within the pumping chamber is not constant. As the pumping chamber undergoes pressure changes during a pumping cycle, the volume of the air bubbles in the pumping chamber changes in response to the changing pressure conditions. Thus, the volume of the air bubbles retained in the pumping chamber of prior art cassettes is not constant and is extremely difficult to compensate. The lobes in the present invention substantially reduce the amount of retained air, thereby greatly reducing the errors caused by retained air.

In addition to removing air bubbles during pumping by dislodging air bubbles adhering to the side walls of the pumping chamber, the lobes also improve the accuracy of fluid delivery by reducing the residual volume of the pumping chamber. Ideally, when a plunger is in the fully extended position, the elastomeric membrane is displaced into the pumping chamber sufficiently to fully displace all of the liquid previously contained therein. Practically speaking, material and structural limitations prevent this ideal result from being achieved. Even when the plunger is completely extended, and the elastomeric membrane is fully displaced into the pumping chamber, some "residual volume" exists. It is in this residual volume that the air bubbles can be trapped. If no residual volume existed, then air could not be trapped and retained in the pumping chamber. By reducing the residual volume, the available volume in which air can be retained is reduced, and the accuracy of the fluid volume delivered is improved.

Empirical studies have shown that given a residual volume of "X," only half of "X" will at any time be occupied by an air bubble. In cassette 10, the residual volume (without lobes 42, and with the plunger in the fully extended position and the membrane fully displaced into the pumping chamber) is approximately 22 $\mu$l, the nominal pumping chamber volume (with the plunger in the home position, and the membrane not displaced into the pumping chamber) is 97 $\mu$l, and the desired delivery volume per pump cycle is 75 $\mu$l. If half of the residual volume of is filled with air, then approximately 11 $\mu$l of air will be contained in the pump chamber after the medicinal liquid has been delivered. As the plunger is retracted, the pressure in the pumping chamber changes, and the 11 $\mu$l air bubble (or multiple air bubbles having an aggregate volume of 11 $\mu$l) expands because the pressure in the pumping chamber is reduced. With the plunger at the home position, the 11 µl volume of air expands to approximately 18 µl. This expansion introduces a 7 µl error (i.e., the difference between 18 µl and 11 µl). Given a desired fluid delivery volume of only 75 µl, this error in volume represents close to a 10% error, which is clearly undesirable.

In the preferred embodiment of the cassette, lobes 42 reduce the residual volume by approximately 4 µl. Thus the residual volume is only 18 µl, and the maximum volume of air likely to be trapped is approximately 9 µl. This approximately 9 µl of air can be expected to expand as described above to approximately 15 µl, introducing an error of approximately 6 µl, rather than the 7 µl error noted above. Thus, without any improvement due to the sweeping action of the lobes, the error is reduced by more than 14% just by the volume of the lobes reducing the residual volume. In the preferred embodiment of the invention, a ridge is included in the pumping chamber proximate the outlet valve (as will be described in detail below in conjunction with FIG. 15), and this ridge reduces the residual volume further by approximately 4 µl. The error reduction provided by reducing the residual volume using the ridge and the lobes is approximately 28%. The actual error reduction is believed to be even more significant due to the sweeping action of the lobes, which assists in removing air bubbles from the walls of the pumping chamber.

FIGS. 6A–6C illustrates elastomeric membrane 20 in phantom detail, with lobe areas 42 shown as shaded to highlight the lobe structure portion of the elastomeric membrane.

Turning now to FIG. 7A, a cross-sectional view of an assembled cassette 10 shows base 18, facing member 22, with elastomeric membrane 20 sandwiched between the base and the facing member. This Figure is a simplified cross-sectional view, because all of the detail included within cross-sectional views 5A and 5B has not been shown (such as inlet valve flap 32), so that the function of lobes 42 can be more clearly illustrated. A plunger 46, driven by a pump unit (not shown) is shown in a retracted or home position, such that elastomeric membrane 20 is not being displaced into pumping chamber 48. Air bubbles 44 are shown adhering to the walls of pumping chamber 48. Lobes 42 can be clearly seen on the undersurface of elastomeric membrane 20, but with plunger 46 in its retracted position, lobes 42 are not yet sweeping the sides of pumping chamber 48.

FIG. 7B shows plunger 46 in an advanced position, being applied to force elastomeric membrane 20 into pumping chamber 48. As elastomeric membrane 20 is displaced into pumping chamber 48, lobes 42 sweep the side walls of pumping chamber 48, thereby displacing air bubbles 44 that were attached to the side walls of pumping chamber 48 toward the bottom and center of the pumping chamber. The lobes actually help to define a flattened central passage through the pumping chamber as the elastomeric membrane is fully extended into the pumping chamber. It is through this central passage that the liquid forced from the pumping chamber flows with the highest velocity when the outlet valve is opened. Air bubbles disposed in this portion of the pumping chamber are more likely to be carried with the liquid from the pumping chamber than air bubbles that remain attached to the side walls of the pumping chamber (which occurs in prior art cassettes).

Yet another feature of the present invention is an integral support on the base, which minimizes movement of a distal delivery tube. It should be noted that the preferred embodiment of the cassette does not include any sensors disposed within the cassette. Instead, the sensors are associated with the pump drive mechanism and are disposed outside of the cassette, e.g., adjacent to a distal delivery tube. Locating sensors external to the disposable cassette enables its size to be minimized, as well as reducing its overall cost. However, because the sensors are not fixedly attached to the cassette structure, movement of the distal delivery tube relative to the external sensors can produce erroneous sensor readings. These erroneous sensor readings can in turn trigger erroneous alarm signals, falsely indicating to a user that there is a condition which needs to be corrected. To minimize the possibility of such false alarms, tube support 16 has been molded into base 18, thereby effectively trapping the distal tube between the drive mechanism and the tube support in one direction and between the sensor components in a transverse direction (see FIG. 10, which is discussed below).

As evident in. FIG. 8, tube support 16 is fabricated from a web-like structure, to reduce material cost and weight of the cassette without sacrificing strength. Those of ordinary skill in the art will readily understand that conventional injection-molding fabrication techniques are applicable in producing the webbing used in tube support 16, as well as the base and facing member. FIG. 9 illustrates a side elevational view of the distal portion of base 18, illustrating further details of outlet 14 and tube support 16. The size of tube support 16 is a function of the size of the distal delivery tube. Preferably tube support 16 is of a size and shape that accommodates and provides support to the size of distal delivery tubes to be used. A distal delivery tube 50 is shown in phantom view in FIG. 9, to illustrate how tube support 16 functions to support one side of the distal delivery tube.

FIG. 10 illustrates disposable cassette 10, a pump unit 54, and a plurality of sensor components 112 that contact distal delivery tube 50. The distal tube is effectively captured between the sensor components, tube support 16, and the pump unit, to ensure that the distal delivery tube 50 does not move relative to the sensor components, thereby causing erroneous sensor readings. One side of distal delivery tube 50 (e.g., the bottom as shown) is supported by tube support 16 (see FIG. 9), and the opposite side of distal delivery tube 50 (e.g., the top as shown) is supported by a corresponding tube support section (not separately shown) included in pump unit 54. The right-hand and left-hand sides of distal delivery tube 50 are supported by sensor components 112. In FIG. 10, the disposition of these components relative to distal delivery tube 50 is clearly illustrated. It should be understood that when properly positioned, tube support 16 of pump cassette 10, sensors 112, and the corresponding tube support for pump unit 54 physically touch distal delivery tube 50, preventing the distal delivery tube from moving while the pump unit and cassette are in operation.

Another important aspect of the present invention involves the inlet and outlet valve flaps that depend from the elastomeric membrane, and the corresponding valve seating surfaces formed in the base. FIG. 11 shows elastomeric membrane 20 seated in base 18, but the valve flaps are not visible in this view since they depend from the opposite or inwardly facing surface of the elastomeric membrane. However, in FIG. 12, a portion of the fluid path between the inlet and outlet formed by the elastomeric membrane and the base is shown and in addition, inlet valve flap 32 and outlet valve flap 34 are illustrated. The lobes described earlier are not shown. It should be understood that the lobes can be incorporated into a cassette independently of the features described below that relate to the valve flaps and valve seating surfaces, although a preferred embodiment of the cassette includes all aspects of the present invention described herein. A portion of plunger 46 is shown in a retracted position, such that elastomeric membrane 20 is not being forced into pumping chamber 48.

Note that outlet valve flap 34 is shown in a partially open position, such that fluid from the pumping chamber can pass through the outlet valve and flow toward outlet 14. A portion of flow stop 24 is also shown. As described in the prior art references earlier cited and incorporated herein by reference, flow stop 24 can be set to ensure that outlet valve flap 34 is in a closed position, and that the fluid flow is stopped. When flow stop 24 exerts a force downwardly against elastomeric membrane 20, the resulting deformation of the elastomeric membrane causes outlet valve flap 34 to fully engage the adjacent valve seating surface 75 formed in base 18 (see FIGS. 12 and 15), thus preventing any fluid from exiting pumping chamber 48 past outlet valve flap 34.

Figure 14:
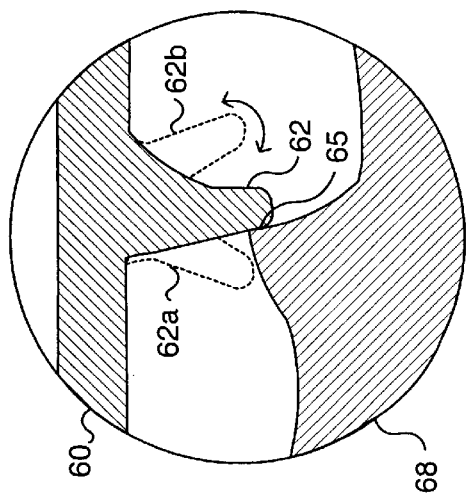
FIG. 14 is an enlarged cross-sectional view of a prior art inlet valve used in a disposable cassette.
Figure 16:
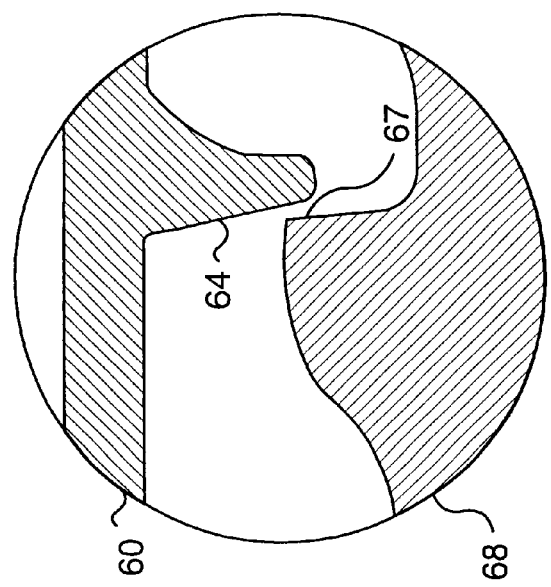
FIG. 16 is an enlarged cross-sectional view of a prior art outlet valve used in a disposable cassette.
Figure 15:
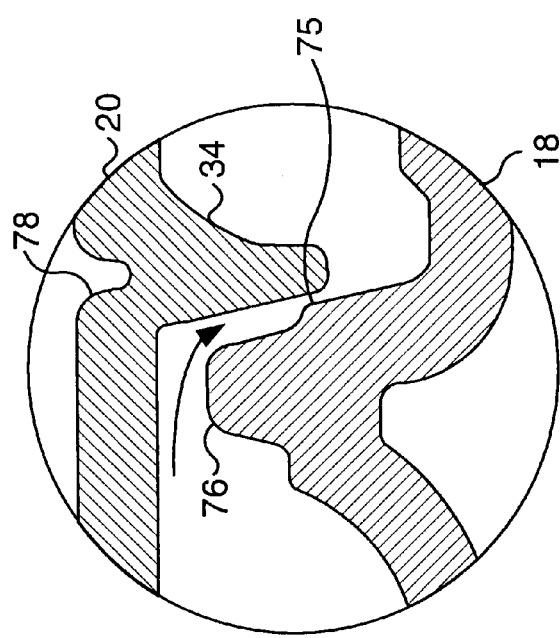
FIG. 15 is an enlarged cross-sectional view of the outlet valve portion of FIG. 12.

Two circular areas in FIG. 12, one encompassing inlet valve flap, and the other encompassing outlet valve flap 34 are shown in greater enlarged detail in FIGS. 13 and 15, respectively. Thus FIG. 13 shows an enlarged view of inlet valve flap 32 and a valve sealing surface 74 on base 18. FIG. 14 illustrates a prior art inlet valve flap 62 and a valve sealing surface 65 described in the above-cited and incorporated references. FIG. 15 shows an enlarged view of outlet valve flap 34 and valve sealing surface 75 on base 18, while FIG. 16 illustrates a prior art outlet valve flap 64 and a valve sealing surface 67 that is described in the above cited references, which have been incorporated by reference herein.

Figure 13B:
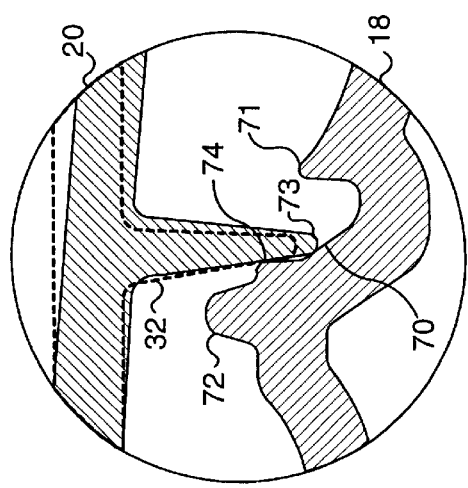
FIGS. 13A and 13B are enlarged cross-sectional views of the inlet valve portion of the cross sectional view of FIG. 12.
Figure 13A:
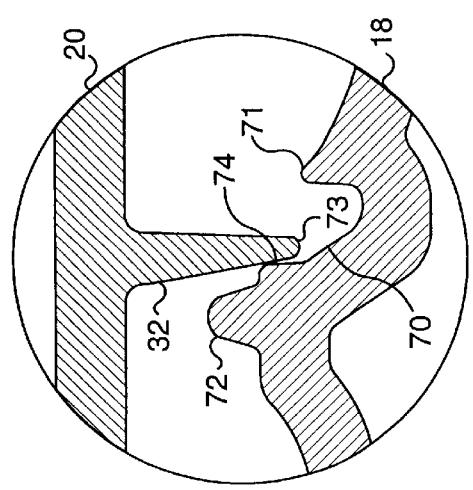

Comparing FIGS. 13A, 13B, and 14, it is clear that inlet valve sealing surface 74 on base 18 is substantially different than an inlet valve sealing surface 65 on prior art base 68. Base 18 includes a valve stop 72, a ramp 70, and a raised lip 71 that are absent from prior art back plate 68. Raised lip 71 further reduces the residual volume in the pumping chamber. The functions of valve stop 72 and ramp 70 are described below.

Valve stop 72 is included to prevent inlet valve flap 32 from being "blown" past the sealing surface by excessive pressure in the pumping chamber. For example, if the inlet to the prior art cassette, which includes an elastomeric membrane 60, base 68, inlet valve flap 62 and valve seat 64, were placed in fluid communication with a source of vacuum, or a low pressure region, inlet valve 62 could be drawn past valve seat 64 in the proximal direction, toward the inlet of the cassette, as is illustrated by the phantom view of an inlet valve flap 62a. When the inlet valve flap is forced into such a position, the cassette becomes non-functional. Valve stop 72 on base 18 prevents inlet valve flap 32 from being forced in the proximal direction past valve sealing surface 74 (or blown). By preventing a "blown inlet valve," valve stop 72 helps to ensure that cassette 10 is more reliable than prior art cassettes.

Ramp 70 is provided for a different purpose in the present invention. In cassettes utilizing the prior art inlet valve illustrated in FIG. 14, when inlet valve flap 62 is in the open position, as indicated by the phantom view of an inlet valve flap 62b, the extreme tip of the inlet valve tends to oscillate back and forth in the liquid flow (see arrows), generating a distinctive audible noise and vibration. Including ramp 70 in the present invention prevents inlet valve flap 32 from similarly oscillating, thus providing a quieter operating cassette. In FIG. 13A, elastomeric membrane 20 is not yet displaced into the pumping chamber, and an extreme tip 73 of the inlet valve is free to oscillate. In FIG. 13B, elastomeric membrane 20 is being displaced into the pumping chamber, and inlet valve flap 32 is forced downwardly. Note that extreme tip 73 now engages ramp 70, preventing any oscillation from occurring. Note further that fluid is free to flow around the peripheral sides of inlet valve flap 32 when it is in this open position, and ramp 70 does not interfere with the flow of medicinal fluid moving past inlet valve flap 32, into pumping chamber 48. Besides reducing audible noise associated with prior art inlet valves, ramp 70 reduces a cracking pressure associated with inlet valve flap 32 when plunger 46 is in the full extended position (displacing elastomeric membrane 20 into pumping chamber 48 to the maximum extent possible) and thus helps to avoid the formation of air bubbles in the pumping chamber due to cavitation in the medicinal liquid, since the velocity of the liquid entering the pumping chamber is less.

FIGS. 15 and 16 illustrate differences between the outlet valves of the present invention and the prior art. Base 18 incorporates a ridge 76 that is not present on prior art base 68. As noted above, ridge 76 and lobes 42 reduce the volume of air bubbles retained within pumping chamber 48, in part, by reducing the residual volume of the pumping chamber. Ridge 76 also increases a velocity of fluid exiting the pumping chamber via outlet valve flap 34. Preferably ridge 76 increases fluid velocity by approximately 25%. This increase in fluid velocity helps to remove air bubbles from the pumping chamber proximate the region of increased fluid flow (see arrows). The higher fluid velocity helps overcome the surface tension that adheres the air bubbles to the walls of the pumping chamber. Note that this increased fluid velocity should help to ensure that any air bubbles removed from the sides of pumping chamber 48 by lobes 42 do not become reattached elsewhere in the pumping chamber, but are instead entrained in the high velocity liquid flow and discharged from the pumping chamber.

Elastomeric membrane 20 preferably includes a core cavity 78 disposed within the outlet flap (best seen in FIG. 15) that is not present in prior art elastomeric membrane 60. Core cavity 78 is produced by eliminating a portion of the material comprising elastomeric membrane 20 in the interior of outlet valve flap 34, which has the effect of changing a "cracking pressure" at which outlet valve flap begins to open. Preferably, the cracking pressure is more than 4 pounds per square inch (PSI), and less than 8 PSI. Using a cracking pressure that is greater than 4 PSI value ensures that outlet valve flap 34 acts as an anti-siphon valve, preventing medicinal liquid from freely flowing through the cassette from its reservoir of other source. Prior art cassette pumps have included ball type anti-siphon valves to prevent the free flow of liquid. Pressure in excess of 8 PSI has empirically been shown to reduce pumping accuracy. An average cracking pressure of 6 PSI is most preferred. It should be noted that other methods of controlling the cracking pressure, besides the incorporation of core cavity 78, could also be used. For example, flow stop 24 (see FIG. 12) exerts a force on the elastomeric membrane proximate outlet valve flap 34. Thus, flow stop 24 can be used to manipulate the cracking pressure of outlet valve flap 34. Note that in FIG. 4D, it appears as if core cavity 78 actually comprises two adjacent depressions because of the slight curvature of core cavity 78, which can be seen in its entirety in FIG. 11.

Core cavity 78 also provides a benefit during the production of elastomeric membrane 20. As those of ordinary skill in the art of injection molding will readily appreciate, such core features are used to provide an outlet for gas bubbles that might otherwise be trapped in the molding material, where they can form imperfections such as undesired voids in the finished product.

Referring now to FIGS. 13 and 15, it can be seen that the base of inlet valve flap 32 is substantially thinner than that of outlet valve flap 34. Those of ordinary skill in the art will appreciate that the relative thickness of a flap type valve at its base affects a cracking pressure at which the valve will begin to open. Thus, modifying the structure and configuration of outlet valve flap 34 enables the cracking pressure of the outlet valve to be controlled. Preferably, the thickness of outlet valve flap 34 and the effect of core cavity 78 are selected to provide a cracking pressure of greater than 4 PSI and less than 8 PSI.

Finally, referring once again to FIGS. 4C and 4D, it can be seen that the shapes of inlet valve flap 32 and outlet valve flap 34 are different. Inlet valve flap 32 has a circular tip, while outlet valve flap 34 has a blunt, flat tip. The blunt, flat tip of outlet valve flap 34 reduces noise generated by an oscillation that would occur as fluid passes through a circular tipped outlet valve. Note that inlet valve flap 32 will not oscillate and generate noise, even though inlet valve flap 32 does have a circular tip, because ramp 70 prevents oscillation and the concomitant audible noise from occurring.

Although the present invention has been described in connection with the preferred form of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A cassette that is adapted to engage a drive mechanism, for use in infusing a fluid into a patient, comprising:
   (a) a housing having a base on which is mounted a facing member, a fluid path being defined at least in part by the base and extending through the cassette between an inlet port and an outlet port, said fluid path including:
      (i) an inlet passage coupled in fluid communication with the inlet port;
      (ii) an outlet passage coupled in fluid communication with the outlet port; and
      (iii) a pumping chamber disposed between the inlet passage and the outlet passage; and
   (b) an elastomeric membrane that extends over the fluid path and when displaced into the pumping chamber, is adapted to force a fluid from the pumping chamber, said elastomeric membrane including a substantially T-shaped lip extending around and proximate its peripheral edge, said T-shaped lip being captured in an interference fit within a groove formed in opposed surfaces of the facing member and the base so that the elastomeric membrane is stretched taut as the facing member is joined to the base, said groove including inclined surfaces that are in interference with corresponding inclined surfaces on said T-shaped lip when the facing member is seated onto and joined to the base with the lip of the elastomeric membrane captured in the groove, a tension in the elastomeric membrane produced by said interference fit due to an interaction of the inclined surfaces of the groove and the T-shaped lip compensating for any inelastic stretching of the elastomeric membrane occurring when the elastomeric membrane is displaced into the pumping chamber, to thereby reduce errors in achieving a desired volume of a fluid infused by the cassette.

2. The cassette of claim 1, wherein an extent of an area of the elastomeric membrane defined by the inclined surfaces of the T-shaped lip is less than an extent of an area defined in the base and facing member by the inclined surfaces of the groove formed therein.

3. The cassette of claim 1, wherein the facing member is seated against and ultrasonically welded to the base while the T-shaped lip of the elastomeric membrane is compressed in the interference fit within the groove.

4. The cassette of claim 1, wherein the fluid path further includes an inlet valve disposed between the inlet passage and the pumping chamber; and an outlet valve disposed between the pumping chamber and the outlet passage.

5. The cassette of claim 4, wherein said inlet valve comprises an inlet valve surface formed in the base, and an inlet valve flap formed on an undersurface of the elastomeric membrane, said inlet valve flap seating against the inlet valve surface when the inlet valve is closed; and wherein said outlet valve comprises an outlet valve surface formed in the base, and an outlet valve flap formed on the undersurface of the elastomeric membrane, said outlet valve flap seating against the outlet valve surface when the outlet valve is closed.

6. The cassette of claim 5, wherein said inlet valve surface comprises a ramp that is contacted by the inlet valve flap when the inlet valve is open, and wherein said inlet valve flap is substantially thinner than the outlet valve flap, said inlet valve being thus configured to substantially reduce audible noise produced as the inlet valve opens and closes.

7. The cassette of claim 6, wherein the thickness of the outlet valve flap and its disposition relative to the outlet valve surface provide a biasing force tending to keep the outlet valve closed until a fluid pressure in the pumping chamber reaches a predetermined level, said biasing force being selected to prevent siphon free flow of a fluid through the cassette.

8. The cassette of claim 1, wherein the base further includes a tube support member that extends beyond the outlet port and adapted to support a tube that is coupled to the outlet port to receive fluid forced from the cassette, so that the tube remains statically positioned relative to an air-in-line sensor provided on the drive mechanism during use of the cassette.

9. A method for mounting an elastomeric membrane in a cassette used for infusing a fluid into a patient, so as to pre-load the elastomeric membrane under an outwardly directed tension, comprising the steps of:
   (a) providing a generally T-shaped lip extending around and proximate to a peripheral edge of the elastomeric membrane, said T-shaped lip having inclined surfaces extending from where the T-shaped lip extends from a generally planar surface of the elastomeric membrane toward distal tips of the T-shaped lip;
   (b) providing a base and a facing member for the cassette that each include a groove with inclined surfaces shaped and sized to receive a different distal tip of the T-shaped lip in an interference fit;
   (c) positioning a distal tip of the T-shaped lip of the elastomeric membrane in the groove formed in one of the base and the facing member;
   (d) seating the groove formed in the other of the base and the facing member onto an opposite:distal tip of the T-shaped lip;
   (e) pressing the base and the facing member toward each other until the T-shaped lip seats within the grooves formed in the base and the facing member, the interference fit between ;the inclined surfaces of the grooves and the T-shaped lip drawing the elastomeric membrane taut under a pre-load tension; and (f) joining the base and the facing members together in a state achieved by step (e) so that the elastomeric membrane is captured under the pre-load tension between the facing member and the base.

10. The method of claim 9, wherein the step of joining the base and the facing member comprises the step of ultrasonically bonding the facing member to the base.

11. The method of claim 9, wherein the step of providing the T-shaped lip includes the step of molding the lip around a peripheral edge of the elastomeric membrane.

12. The method of claim 9, wherein an area of the elastomeric membrane circumscribed by the lip:is less than an area circumscribed by the grooves formed in both the base and the facing member.

13. The method of claim 9, wherein the step of joining comprises the step of thermally bonding the facing member to the base.

14. The method of claim 9, wherein the step of joining comprises the step of adhesively bonding the facing member to the base.

15. A cassette that is adapted to engage a drive mechanism, for use in infusing a medicinal liquid into a patient, comprising:

(a) a housing having a base on which is mounted a facing member, a fluid path being defined at least in part by the base and extending through the cassette between an inlet port and an outlet port of the cassette, said fluid path including:
  (i) an inlet passage coupled in fluid communication with the inlet port;
  (ii) an outlet passage coupled in fluid communication with the outlet port; and
  (iii) a pumping chamber disposed between the inlet passage and the outlet passage; and (b) an elastomeric membrane that extends over the fluid path and when displaced into the pumping chamber, is adapted to force a fluid from the pumping chamber, said elastomeric membrane having a generally planar undersurface facing toward the base, but including two lobes of increased thickness disposed above the pumping chamber at opposite sides thereof and extending into the pumping chamber, so that when the elastomeric diaphragm is displaced into the pumping chamber by a drive mechanism, the lobes sweep away air bubbles that may be retained on adjacent sides of the pumping chamber, said lobes defining a shallow elongate path through the pumping chamber when the elastomeric membrane is displaced to its full extent into the pumping chamber, so that a substantial portion of any air contained within the pumping chamber is carried out of the pumping chamber with the medicinal liquid being infused.

16. The cassette of claim 15, wherein the elastomeric membrane further includes an inlet valve flap and an outlet valve flap, both of which depend from the undersurface of the elastomeric membrane, the inlet valve flap when closed by a fluid pressure within the pumping chamber forming a seal against an inlet valve surface formed in the base and disposed between the inlet passage and the pumping chamber, and the outlet valve flap when closed, forming a seal against an outlet valve surface formed in the base and disposed between the pumping chamber and the outlet passage.

17. The cassette of claim 16, wherein the inlet valve is configured to be substantially thinner at a tip than where the inlet valve flap joins with a substantially planar portion of the elastomeric membrane, and wherein the base includes a ramp that contacts the inlet valve flap to prevent it from oscillating and thereby reducing audible noise.

18. The cassette of claim 17, wherein the outlet valve flap is substantially thicker than the inlet valve flap and is configured to provide a biasing force tending to maintain the outlet valve flap sealed against the outlet valve surface until a pressure in the pumping chamber exceeds a predefined cracking level.

19. The cassette of claim 17, wherein the predefined cracking level is selected to prevent a siphon induced free flow of fluid through the cassette.

20. The cassette of claim 15, wherein the base includes a distal member that extends distally past the outlet port and is adapted to support a tube that is coupled in fluid communication with the outlet port, to minimize movement of the tube relative to an air-in-line sensor included on the drive mechanism.

21. A cassette that is adapted to engage a drive mechanism, for use in infusing a medicinal liquid into a patient, comprising:

(a) a housing having a base on which is mounted a facing member, a fluid path being defined at least in part by the base and extending through the cassette between an inlet port and an outlet port, said fluid path including:
  (i) an inlet passage coupled in fluid communication with the inlet port;
  (ii) an outlet passage coupled in fluid communication with the outlet port; and
  (iii) a pumping chamber disposed between the inlet passage and the outlet passage;

(b) an elastomeric membrane that extends over the fluid path and when displaced into the pumping chamber, is adapted to force a fluid from the pumping chamber; and (c) means for reducing a volume of air retained within said pumping chamber when said elastomeric membrane is displaced into the pumping chamber during a pumping cycle.

22. The cassette of claim 21, wherein said means comprises at least one structure disposed within said pumping chamber, said structure occupying a portion of a volume of said pumping chamber, said at least one structure reducing a residual volume of the pumping chamber, thereby reducing a volume of air that can be retained within said pumping chamber during a pumping cycle.

23. The cassette of claim 22, wherein said at least one structure is disposed on at least one of said elastomeric membrane and said base.

24. The cassette of claim 22, wherein said at least one structure is disposed on said elastomeric membrane and extends into the pumping chamber such that when said elastomeric membrane is displaced into the pumping chamber by a drive mechanism, said at least one structure sweeps away any air bubbles that may be retained on adjacent walls of the pumping chamber, so that such air bubbles become entrained within the medicinal liquid and are carried out of the pumping chamber with the medicinal liquid.

25. The cassette of claim 22, wherein said at least one structure is disposed on said base, and said at least one structure further extends into the pumping chamber such that a distance between said at least one structure and said elastomeric membrane is reduced compared to a distance between said base and said elastomeric membrane in other portions of said pumping chamber, thereby increasing a velocity of said medicinal liquid as it passes between said at least one structure and said elastomeric membrane, the medicinal fluid thereby tending to carry away any air bubbles that may be retained on walls of the pumping chamber proximate said at least one structure, said air bubbles becoming entrained within the medicinal liquid and being carried out of the pumping chamber with the medicinal liquid.

26. The cassette of claim 22, wherein said at least one structure reduces said residual volume by at least 18%.

27. The cassette of claim 21, wherein said means comprises at least one lobe disposed on said elastomeric membrane and extending into the pumping chamber, so that when said elastomeric membrane is displaced into the pumping chamber by a drive mechanism, said at least one lobe sweeps away air bubbles that may be retained on a wall of the pumping chamber, the air bubbles becoming entrained within the medicinal liquid and being carried out of the pumping chamber with the medicinal liquid, thereby reducing a volume of air retained within said pumping chamber.

28. A cassette that is adapted to engage a drive mechanism, for use in infusing a medicinal liquid into a patient, comprising:
  (a) a housing having a base on which is mounted a facing member, a fluid path being defined at least in part by the base and extending through the cassette between an inlet port and an outlet port, said fluid path including:
    (i): an inlet passage coupled in fluid communication with the inlet port;
    (ii) an outlet passage coupled in fluid communication with the outlet port; and
    (iii) a pumping chamber disposed between the inlet passage and the outlet passage;
  (b) an elastomeric membrane that extends over the fluid path and when displaced into the pumping chamber, is adapted to force a fluid from the pumping chamber, said elastomeric membrane comprising an inlet valve flap and an outlet valve flap, both of which depend from the undersurface of the elastomeric membrane, the inlet valve flap when closed by a fluid pressure within the pumping chamber forming a seal against an inlet valve surface that is formed in the base and is disposed between the inlet passage and the pumping chamber, and the outlet valve flap when closed, forming a seal against an outlet valve surface that is formed in the base and is disposed between the pumping chamber and the outlet passage; and
  (c) means for reducing an audible noise that is otherwise caused by an oscillation of at least one of the inlet valve flap and the outlet valve flap in response to a flow of medicinal liquid through the cassette.

29. The cassette of claim 28, wherein said means comprises at least one ramp disposed adjacent at least one of said inlet valve flap and outlet valve flap, such that when in an open position, a tip of said at least one of said inlet valve flap and said outlet valve flap engages one of said at least one ramp, thereby preventing said tip from oscillating, and substantially reducing an audible noise that would be generated by such an oscillation.

30. The cassette of claim 28, wherein said at least one of said inlet valve flap and outlet valve flap is configured to open in response to a predetermined pressure.

31. The cassette of claim 28, wherein said means comprises a shape and a configuration of said at least one of the inlet valve flap and the outlet valve flap, said shape and said configuration being selected to produce a minimal oscillation in response to a flow of medicinal liquid passing thereby.

32. The cassette of claim 31, wherein said shape and said configuration include a blunt, flattened tip.

33. The cassette of claim 28, wherein the inlet valve flap is substantially thinner than the outlet valve flap, and wherein the base includes a ramp that is inclined at an angle selected to contact and cooperate with the inlet valve flap in reducing audible noise caused by movement of the inlet valve flap.

34. A cassette that is adapted to engage a drive mechanism, for use in infusing a medicinal liquid into a patient, comprising:
  (a) a housing having a base on which is mounted a facing member, a fluid path being defined at least in part by the base and extending through the cassette between an inlet port and an outlet port, said fluid path including:
    (i) an inlet passage coupled in fluid communication with the inlet port;
    (ii) an outlet passage coupled in fluid communication with the outlet port; and
    (iii) a pumping chamber disposed between the inlet passage and the outlet passage;
  (b) an elastomeric membrane that extends over the fluid path and when displaced into the pumping chamber, is adapted to force a fluid from the pumping chamber, said elastomeric membrane comprising an inlet valve flap and an outlet valve flap, both of which depend from the undersurface of the elastomeric membrane, the inlet valve flap when closed by a fluid pressure within the pumping chamber forming a seal against an inlet valve surface formed in the base and disposed between the inlet passage and the pumping chamber, and the outlet valve flap when closed, forming a seal against an outlet valve surface formed in the base and disposed between the pumping chamber and the outlet passage; and
  (c) means for achieving a predetermined cracking pressure associated with moving said outlet valve flap away from said outlet valve surface.

35. The cassette of claim 34, wherein said means comprises a core cavity disposed in an interior of said outlet valve flap.

36. The cassette of claim 34, wherein said means comprises a selecting a shape and a configuration of the outlet valve flap that determines a force required to move the outlet valve flap away from the outlet valve surface.

37. The cassette of claim 34, further comprising a ridge disposed adjacent to said inlet valve flap to prevent the inlet valve flap from being forced past the inlet valve surface, which would render the cassette inoperative.

38. The cassette of claim 34, wherein said predetermined cracking pressure is in a range of from about 4 PSI to about 8 PSI.

* * * * *

UNITED STATES PATENT AND TRADEMARK OFFICE
CERTIFICATE OF CORRECTION

PATENT NO.    : 6,494,694 B2
DATED         : December 17, 2002
INVENTOR(S)   : Mike W. Lawless et al.

It is certified that error appears in the above-identified patent and that said Letters Patent is hereby corrected as shown below:

Column 17,
Line 2, delete ";".
Line 16, delete ":".

Column 19,
Line 28, delete ":" after (i).

Signed and Sealed this

Twenty-second Day of July, 2003

JAMES E. ROGAN
*Director of the United States Patent and Trademark Office*